(12) United States Patent
Edwards (10) Patent No.: US 10,266,904 B2
(45) Date of Patent: Apr. 23, 2019

(54) SYNTHETIC LONG READ DNA SEQUENCING

(71) Applicant: STC.UNM, Albuquerque, NM (US)

(72) Inventor: Jeremy Scott Edwards, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 345 days.

(21) Appl. No.: 15/027,069

(22) PCT Filed: Sep. 24, 2014

(86) PCT No.: PCT/US2014/057260
§ 371 (c)(1),
(2) Date: Apr. 4, 2016

(87) PCT Pub. No.: WO2015/053943
PCT Pub. Date: Apr. 16, 2015

(65) Prior Publication Data
US 2016/0244811 A1    Aug. 25, 2016

Related U.S. Application Data

(60) Provisional application No. 61/888,780, filed on Oct. 9, 2013.

(51) Int. Cl.
*C12Q 1/68* (2018.01)
*C12Q 1/689* (2018.01)
*C12Q 1/6853* (2018.01)

(52) U.S. Cl.
CPC ............ *C12Q 1/689* (2013.01); *C12Q 1/6853* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2011/0033854 A1* | 2/2011 | Drmanac et al. | C12P 19/34 435/6.12 |
| 2012/0024701 A1 | 2/2012 | Montagnier et al. | |
| 2016/0244811 A1 | 8/2016 | Edwards | |

FOREIGN PATENT DOCUMENTS

| | | |
|---|---|---|
| WO | WO 2013/019075 A2 | 2/2013 |
| WO | WO 2013/096802 A1 | 6/2013 |
| WO | WO 2015/053943 A1 | 4/2015 |

OTHER PUBLICATIONS

U.S. Appl. No. 61/888,780, filed Oct. 9, 2013, Jeremy Scott Edwards.

(Continued)

*Primary Examiner* — Kaijiang Zhang
(74) *Attorney, Agent, or Firm* — Mueting, Raasch & Gebhardt, P.A.

(57) ABSTRACT

The disclosure describes a method for sequencing long portions of DNA sequence by assembling a plurality of shorter polynucleotide reads. Generally, The method includes annealing a plurality of primers to a denatured DNA molecule, appending a barcode polynucleotide to the 5' end of the primer, subjecting the DNA molecules to a plurality of cycles of (1) pooling, (2) dividing, and (3) appending a barcode polynucleotide to the 5' end of the primer, sequencing the barcode polynucleotides and the genomic DNA, and assembling the short read polynucleotide sequences having identical barcode polynucleotides.

6 Claims, 6 Drawing Sheets

Specification includes a Sequence Listing.

Method

Anneal random primer to single stranded DNA — Extend with DNA polymerase — Add bar-coded primer — Amplify 4-5 cycles (56) References Cited

OTHER PUBLICATIONS

Kim et al., "'Shotgun DNA synthesis' for the high-throughput construction of large DNA molecules" Jun. 2012 *Nucleic Acids Research*, 40(18):1-8.
Magoc et al., "FLASH: fast length adjustment of short reads to improve genome assemblies" 2011 *Bioinformatics*, 27(21):2957-2963.
Peters et al., "Accurate whole-genome sequencing and haplotyping from 10 to 20 human cells" Jul. 2012 *Nature*, 487:190-195.
International Patent Application No. PCT/US2014/057260, filed Sep. 24, 2014; International Search Report and Written Opinion dated Jan. 2, 2015; 14 pages.
International Patent Application No. PCT/US2014/057260, filed Sep. 24, 2014; International Preliminary Report on Patentability dated Apr. 21, 2016; 9 pages.
European Patent Application No. 14852570.2, filed Sep. 24, 2014; Supplementary Search Report dated Apr. 7, 2017; 10 pages.

\* cited by examiner

Barcode 3   Barcode 2   Barcode 1   Common Sequence   Random 10mer
CGATACACCCAACACGCTCACGTACCCAGTGATAGGAGTGCACTGAGCTCGTACTCTCAATCCNNNNNNNNNN
GCTATGTGGGTTGTGCGAGTCCATGGTCACTATCCTCACGTGACTCGAGC

Fig. 7

CGATACACCCAACACGCTCACGTACCCAGTGATAGGAGTGCACTGAGCTCGTACTCTCAATCCGTGAATATAC
TGGCGGTTGGTTGGTCGGGGAGGGGAATTATCAGGATTACTGCACAACACCCCTGCGGAAATTCCTCT
GGATCAAAAACTCACCC

ID
NO:6) binds to a portion of the genome; common sequence
SYNTHETIC LONG READ DNA SEQUENCING

CROSS-REFERENCE TO RELATED APPLICATION

This application is the § 371 U.S. National Stage of International Application No. PCT/US2014/057260, filed 24 Sep. 2014, which claims priority to U.S. Provisional Patent Application Ser. No. 61/888,780, filed Oct. 9, 2013, each of which is incorporated herein by reference.

SEQUENCE LISTING

This application contains a Sequence Listing electronically submitted to the United States Patent and Trademark Office via EFS-Web as an ASCII text file entitled "2014-09-24-SequenceListing_ST25.txt" having a size of 4 KB and created on Sep. 22, 2014. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein and does not go beyond the disclosure in the International Application as filed.

SUMMARY

In one aspect, this disclosure describes a method that includes denaturing a plurality of DNA molecules; attaching a plurality of primers to the denatured DNA molecules, so that the DNA molecules have a plurality of sites to which a primer is attached; dividing the DNA molecules into a plurality of chambers; adding a polynucleotide barcode to one end of at least a portion of the primers; pooling the samples from at least a plurality of the chambers; redistributing the pooled samples into a second plurality of chambers; repeating adding a polynucleotide barcode to the end of at least a portion of the primers and pooling the samples; sequencing the genomic DNA and the polynucleotide barcode; and assembling the plurality of short reads having identical barcodes into a single long read synthetic polynucleotide sequence.

In some embodiments, the polynucleotide barcode comprises at least five nucleotides.

In some embodiments, the method can include 2-8 repeat cycles.

In some embodiments, the method can further include extending primers attached to the DNA molecule with a polymerase prior to dividing the DNA molecules into the plurality of chambers.

In some embodiments, the polynucleotide barcode is added to the 5' end of at least a portion of the primers.

In another aspect, this disclosure describes a polynucleotide that includes a 3' region comprising a randomized sequence of nucleotides; an amplification sequence 5' to the 3' region that is complementary to an amplification primer; and a 5' region 5' to the amplification sequence. In some embodiments, the 3' region includes from five to 25 nucleotides. In some embodiments, the amplification sequence can include from six to 50 nucleotides. In some embodiments, the 5' region can include from one to 10 nucleotides

DETAILED DESCRIPTION OF ILLUSTRATIVE EMBODIMENTS

This disclosure describes a method for generating long read DNA sequences. Currently, ultra-high throughput sequencing technologies typically generate short reads of less than 250 bases. Reads of up to 250 bases are typically too short to answer many biological questions. For example, these read lengths are too short to phase variants on homologous chromosomes, efficiently find structural variation and rearrangements in the genome, or perform de novo sequencing. The method described herein allows for "synthetic" long reads. Namely, we are able to piece short reads together to generate a long read.

Thus, the methods described herein provide a technology that allows short read DNA sequencing to be used for full de novo genome sequencing. Currently it is not possible assemble a mammalian sized genome using short read next generation sequencing technology to a quality consistent with the human genome reference sequence. The methods described herein generally involve scaffolding short reads into a synthetic long read. The synthetic long reads that can be generated can be of a DNA sequence of any length. In certain embodiments, the methods can generate a synthetic long read of a DNA sequence having a length of at least 500 base pairs (bp) such as, for example, at least 700 bp, at least 1 kilobases (kb), at least 10 kb, at least 50 kb, at least 100 kb, at least 500 kb, up to and including the length of an entire chromosome. If the synthetic read is shorter than the entire chromosome, the sub-chromosomal synthetic reads can be assembled into complete chromosomes. In particular embodiments, the methods can be used to generate a synthetic long read of a DNA sequence having a length of at least 100 kb.

Figure 1:
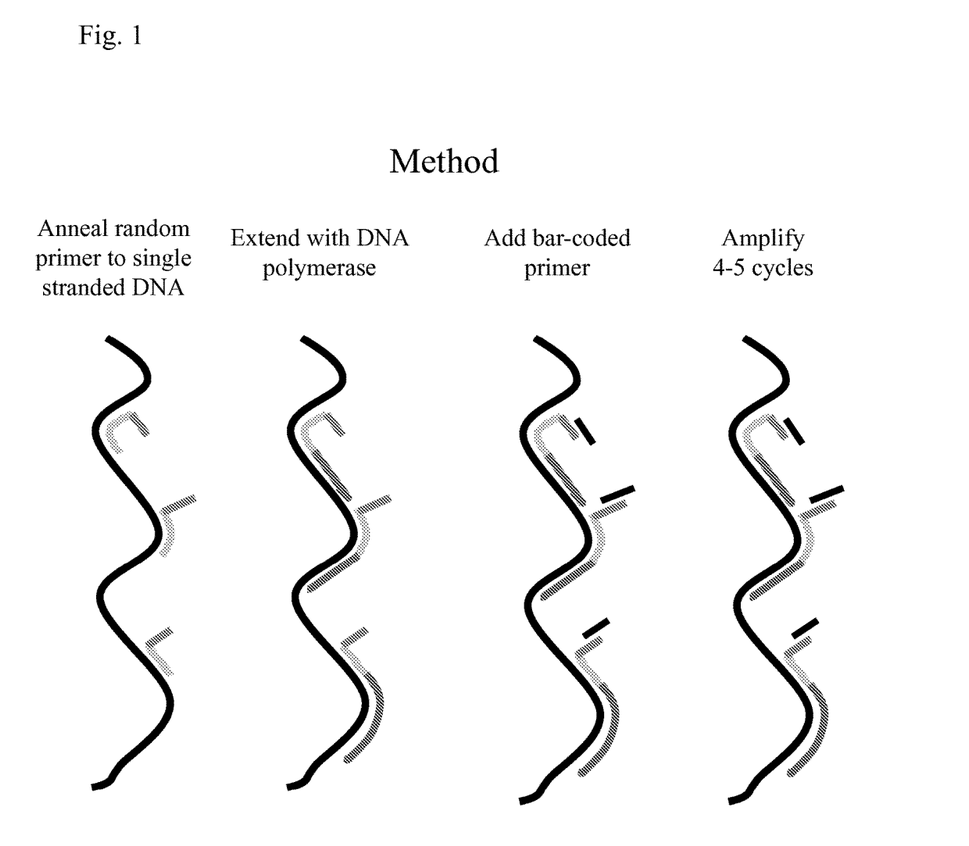
FIG. 1. A schematic diagram illustrating an embodiment of the DNA sequencing method described herein.
Figure 2:
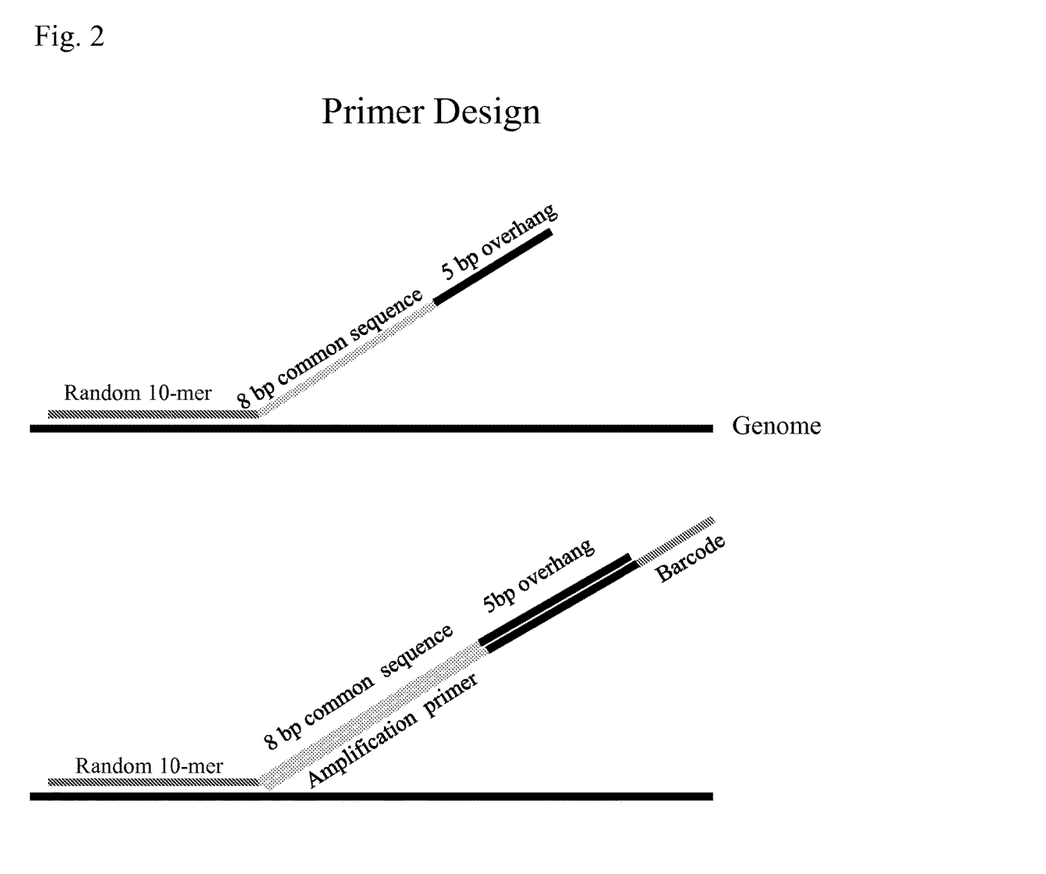
FIG. 2. A schematic diagram illustrating the design of primers for use ion the DNA sequencing method described herein.

A generalized depiction of the methods is illustrated in FIG. 1. The isolated DNA is denatured and primers that randomly prime the genome are annealed. A generalized primer design is illustrated in FIG. 2. Each primer contains a random sequence region at the 3' end that allows for random priming of the genome, a common sequence for amplifying the primer, and a 5' sequence that allows for building a barcode off the 5' end of the primer.

While the primer is illustrated in FIG. 2 and described in detail below in an orientation in which the 3' end of the primer anneals to a genomic sequence and the barcode is built from the 5' end of the primer, a primer may alternatively have the opposite orientation—i.e., the 5' end of the primer may anneal to a genomic sequence and the barcode may be built from the 3' end of the primer.

In the embodiment illustrated in FIG. 2, the 3' end of the primer is 10 nucleotides in length. The 3' end of the primer designed to anneal to the genome can be, however, of any desired length. Thus, the 3' end of the primer can have a minimum length of at least four nucleotides such as, for example, at least five nucleotides such as, for example, at least six nucleotides, at least seven nucleotides, at least eight nucleotides, at least nine nucleotides, at least 10 nucleotides, at least 11 nucleotides, at least 12, nucleotides, at least 15 nucleotides, or at least 20 nucleotides. The 3' end of the primer may have a maximum length of any number of nucleotides that can be synthesized with accuracy and precision. In some embodiments, the 3' end can have a maximum length of no more than 100 nucleotides such as, for example, no more than 50 nucleotides, no more than 25 nucleotides, no more than 12 nucleotides, no more than 11 nucleotides, no more than 10 nucleotides, no more than nine nucleotides, no more than eight nucleotides, no more than seven nucleotides, or no more than six nucleotides. The 3' end of the primer may have a length defined by a range having as endpoints any minimum length listed above and any maximum length that is greater than the minimum length. In various embodiments, the 3' end of the primer can have a length of from six to 10 nucleotides. In other embodiments, the 3' end of the primer can have a length of from six to nine nucleotides. In particular embodiments, the 3' end of the primer can have a length of six nucleotides, seven nucleotides, eight nucleotides, nine nucleotides, or 10 nucleotides. The sequence of this 3' end of the primer is random so that the methods can cover the entirety of the DNA sequence being sequenced.

The embodiment illustrated in FIG. 2 shows the common sequence having a length of eight nucleotides. The common sequence can, however, be of any suitable length. Thus, the common sequence can have a minimum length of at least six nucleotides such as, for example, at least seven nucleotides, at least eight nucleotides, at least nine nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides. The common sequence can have a maximum length of no more than 100 nucleotides such as, for example, no more than 50 nucleotides, no more than 30 nucleotides, no more than 25 nucleotides, no more than 24 nucleotides, no more than 23 nucleotides, no more than 22 nucleotides, no more than 21 nucleotides, no more than 20 nucleotides, no more than 19 nucleotides, no more than 18 nucleotides, no more than 17 nucleotides, no more than 16 nucleotides, no more than 15 nucleotides, no more than 14 nucleotides, no more than 13 nucleotides, no more than 12 nucleotides, no more than 11 nucleotides, no more than 10 nucleotides, or no more than nine nucleotides. The common sequence can have a length defined by a range having as endpoints any minimum length listed above and any maximum length that is greater than the minimum length. In some embodiments, the common sequence can have a length of from eight to 22 nucleotides such as, for example, from eight to 15 nucleotides. In particular embodiments, the common sequence can have a length of eight nucleotides, nine nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, or 22 nucleotides. The common sequence is designed to be complementary to the amplification primer selected for amplifying the primer annealed to the DNA. The amplification primer should be designed to have an appropriate melting temperature (Tm) for amplification, and not have complementarity to regions within the human genome.

Figure 6:
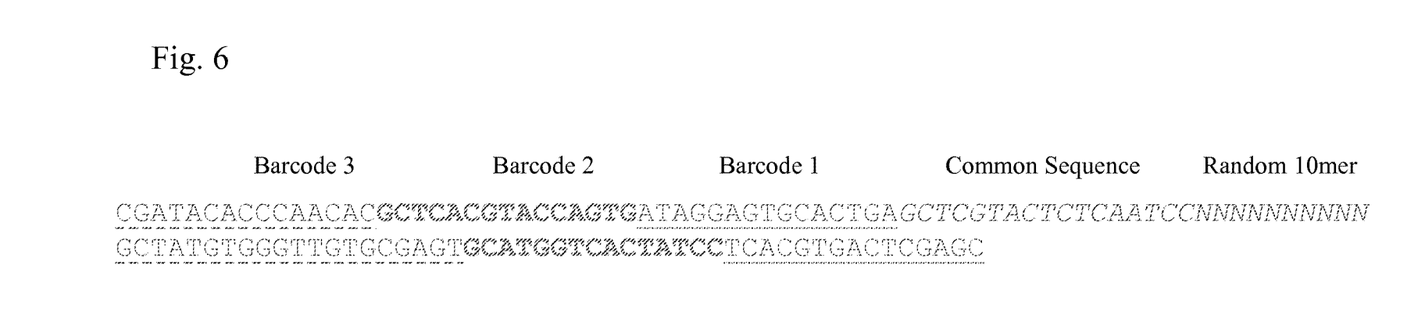
FIG. 6. Exemplary primer (SEQ ID NO:6) and its complementary strand (SEQ ID NO:7) with three exemplary barcodes built off of the 5' end of the primer. 3' random sequence (NNNNNNNNNN; residues 63-72 of SEQ ID NO:6) binds to a portion of the genome; common sequence (italic); barcode 1 (dotted underline); barcode 2 (bold); barcode 3 (dashed underline).

The 5' end of the primer has a sequence that allows building a barcode on the 5' end of the primers in subsequent steps. The 5' end of the primer can include any sequence of nucleotides that allows for building of a barcode. In the embodiments illustrated in FIG. 2 and FIG. 6, the 5' end of the primer has a length of five nucleotides that forms an overhang once an amplification primer is annealed to the common sequence. In other embodiments, however, the 5' end of the primer may be of any suitable length. Thus, the 5' end of the primer can have a minimum length of at least one nucleotide, at least two nucleotides, at least three nucleotides, at least four nucleotides, at least five nucleotides, at least six nucleotides, at least seven nucleotides, or at least eight nucleotides. The 5' end of the primer can have a maximum length of no more than 100 nucleotides such as, for example, no more than 50 nucleotides, no more than 25 nucleotides, no more than 15 nucleotides, no more than 14 nucleotides, no more than 13 nucleotides, no more than 12 nucleotides, no more than 11 nucleotides, no more than ten nucleotides, no more than nine nucleotides, no more than eight nucleotides, no more than seven nucleotides, no more than six nucleotides, no more than five nucleotides, no more than four nucleotides, no more than three nucleotides, or no more than two nucleotides. The 5' end of the primer can have a length defined as range having as endpoints any minimum length listed above and any maximum length that is greater than the minimum length. In some embodiments, the 5' end of the primer can have a length of from one to eight nucleotides such as for example, from one to five nucleotides, from four to eight nucleotides, or from five to seven nucleotides. In particular embodiments, the 5' end of the primer can have a length of one nucleotide, two nucleotides, three nucleotides, four nucleotides, five nucleotides, six nucleotides, seven nucleotides, or eight nucleotides. In one embodiment, for example, the 5' end can have a sequence of -TTTTTTT-5' (SEQ ID NO:1). In another embodiment, however, the 5' portion of the primer was essentially a randomized sequence of -CGTGCAT-5' (SEQ ID NO:2).

Thus, in various embodiments, the primer can be, for example, any of:

(SEQ ID NO: 3)
5-A*A*AAAAVVVVVV*V*V-3, (SEQ ID NO: 4)
5-G*C*ACGTACTCTCAATCCNNNNNNNN*N*N-3,
or (SEQ ID NO: 5)
5-G*C*ACGTACTCTCAATCCNNNNNN*N*N-3, where * indicates a phosphothioate linkage, V is any base except T, and N is any base.

Next, the primers are extended to make the DNA double stranded to reduce the extent to which individual DNA molecules stick together. The methods exploit properties exhibited by individual DNA molecules. The primers may be extended using a polymerase that does not have strand displacement or 5'→3' exonuclease activity, such as PHUSION (New England Biolabs Inc., Ipswich, Mass.), T4, or T7 polymerase. When such a polymerase is used, the extent to which downstream primers are dislodged from the DNA is minimized. However, a polymerase with exonuclease activity such as, for example, Bst DNA polymerase can be used if one uses primers with phosphothioate linkages to limit exonuclease digestion of the primers. If one uses a polymerase with proofreading activity (3'→5' exonuclease activity), one can add phosphothioate linkages on the 3' end of the primers.

Alternatively, one can nick the long template DNA molecules using a nicking enzyme, such as, for example, Nt.BstNBI, Nt.AlwI, Nb.BsrDI, Nt.CviPII, or any other nicking endonuclease that cleaves the DNA on only a single strand. The cleaved strand has a free 3'-OH and a 5'-phosphate, and is amenable to enzymatic operation. The nicked DNA can be directly ligated to a primer that includes a moiety for barcode construction. However, before the ligation, one must do something to prevent the nick from being repaired by the ligase. One can treat the DNA with a phosphatase to remove the 5' phosphate groups and/or create a small gap using an exonuclease. One can then ligate primers that contain the needed 5' extensions to the nicked sites. The polymerase extension can still be performed to ensure the entire molecule is double stranded.

Alternatively, one can randomly introduce dU into the DNA. This can be done prior to the long DNA molecule isolation, or by using a nicking enzyme to introduce nicks, as described above. One can then use a polymerase to introduce labeled bases or dU into the chain using conventional methods. Nicks can then be created by treating the DNA with an enzyme cocktail such as, for example, USER (New England Biolabs, Inc., Ipswich, Mass.), or a combination of Uracil DNA glycosylase (UDG) and the DNA glycosylase-lyase Endonuclease VIII. These nick sites can then be used to attach the 5' labeled primers for building the barcode.

After the dsDNA is successfully prepared and the primers are attached with 5'extensions available for barcode attachment, one can attach a barcode to the extended primer. (FIG. 2). There are multiple methods for building the barcode on the 5' extension. One method for building the barcode is to use ligase to attached barcoded primers to the 5' extension. Alternatively, one can simply hybridize primers to the 5' extension, but not perform the ligation. The hybridization should be sufficient to hold the DNA barcode together as long as the double stranded region is sufficiently long. As another alternative approach, one can chemically synthesize the barcode by reacting to groups on the 5' extension.

Figure 4:
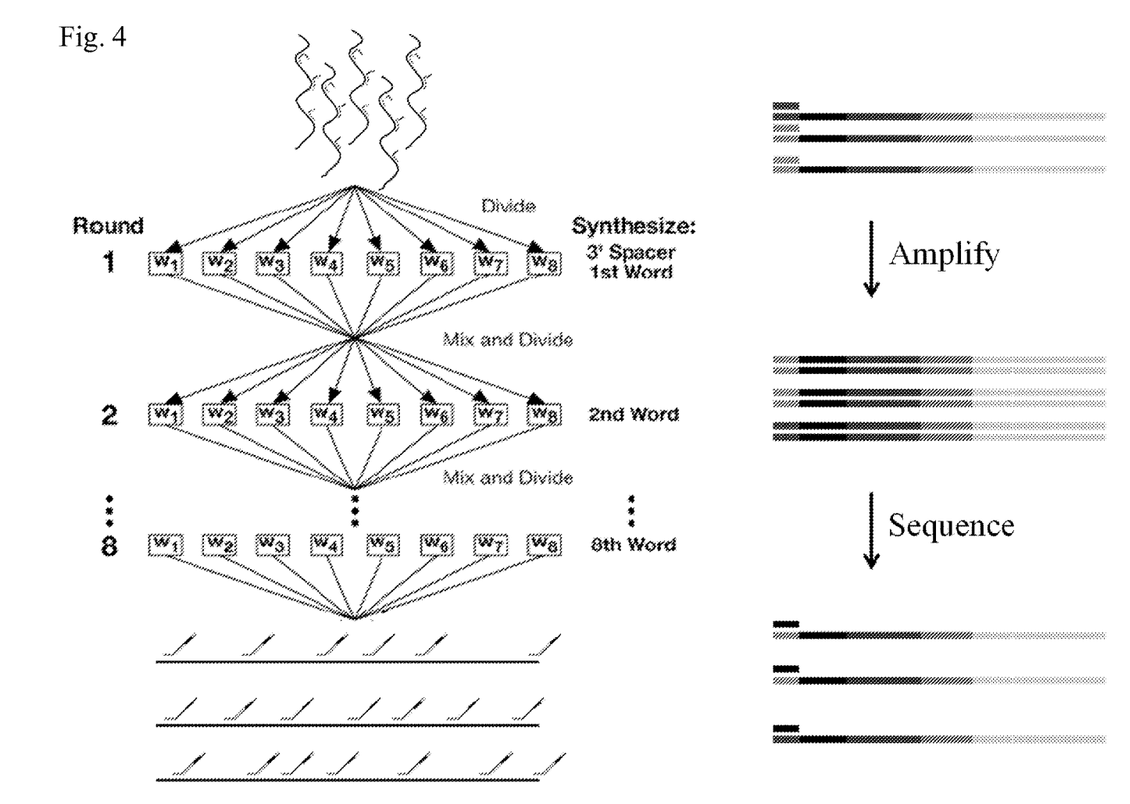
FIG. 4. A diagram illustrating amplification and assembly of short read sequences according to the sequencing method described herein.

To build the entire barcode, any of the chemical or molecular biology methods described above may be used. The general scheme for growing the barcode is illustrated in FIG. 4. First, one can distribute the DNA molecules into the wells of a 96-well plate. One can attach a short barcode sequence to the 5' end of the primers using any one of the approaches described in the immediately preceding paragraph or any other approach that may be used to grow a DNA chain. One can then pool all of the DNA from the 96 wells together. Next, one randomly divides the DNA in the sample into another 96 wells and attaches another barcode sequence onto the 5' end of the primers so that the primers will have two barcode sequences on the 5' end. The pooling and dividing cycle may be repeated as many times as desired. Depending on the application, one can do more or less cycles. As the number of repeat cycles increases, so does the degree to which one generates unique barcodes. The number of distinct barcodes will grow according to the formula $96^N$, where N is the number of cycles for adding to the barcode. Thus, for example, four cycles generates $96^4$=84,934,656 distinct barcodes. The result will be that each long isolated DNA molecule will have a large number of primers. Moreover, each primer on an individual DNA molecule will have the same barcode. Different long DNA molecules will, however, get different barcodes.

In some embodiments, the methods include a minimum of at least two repeat cycles to grow the barcodes such as, for example, at least three repeat cycles, at least four repeat cycles, at least five repeat cycles, at least six repeat cycles, at least seven repeat cycles, or at least eight repeat cycles. In some embodiments, the methods includes a maximum no more than 12 repeat cycles to grow the barcodes such as, for example, no more than 11 repeat cycles, no more than 10 repeat cycles, no more than nine repeat cycles, no more than eight repeat cycles, no more than seven repeat cycles, no more than six repeat cycles, or no more than five repeat cycles. The number of repeat cycles can, in some cases, be expressed as a range having as endpoints any minimum number of repeat cycles listed above and any maximum number of repeat cycles that is greater than the minimum number of repeat cycles. In some embodiments, the methods can include, for example, 4-8 repeat cycles to grow the barcodes.

Figure 3:
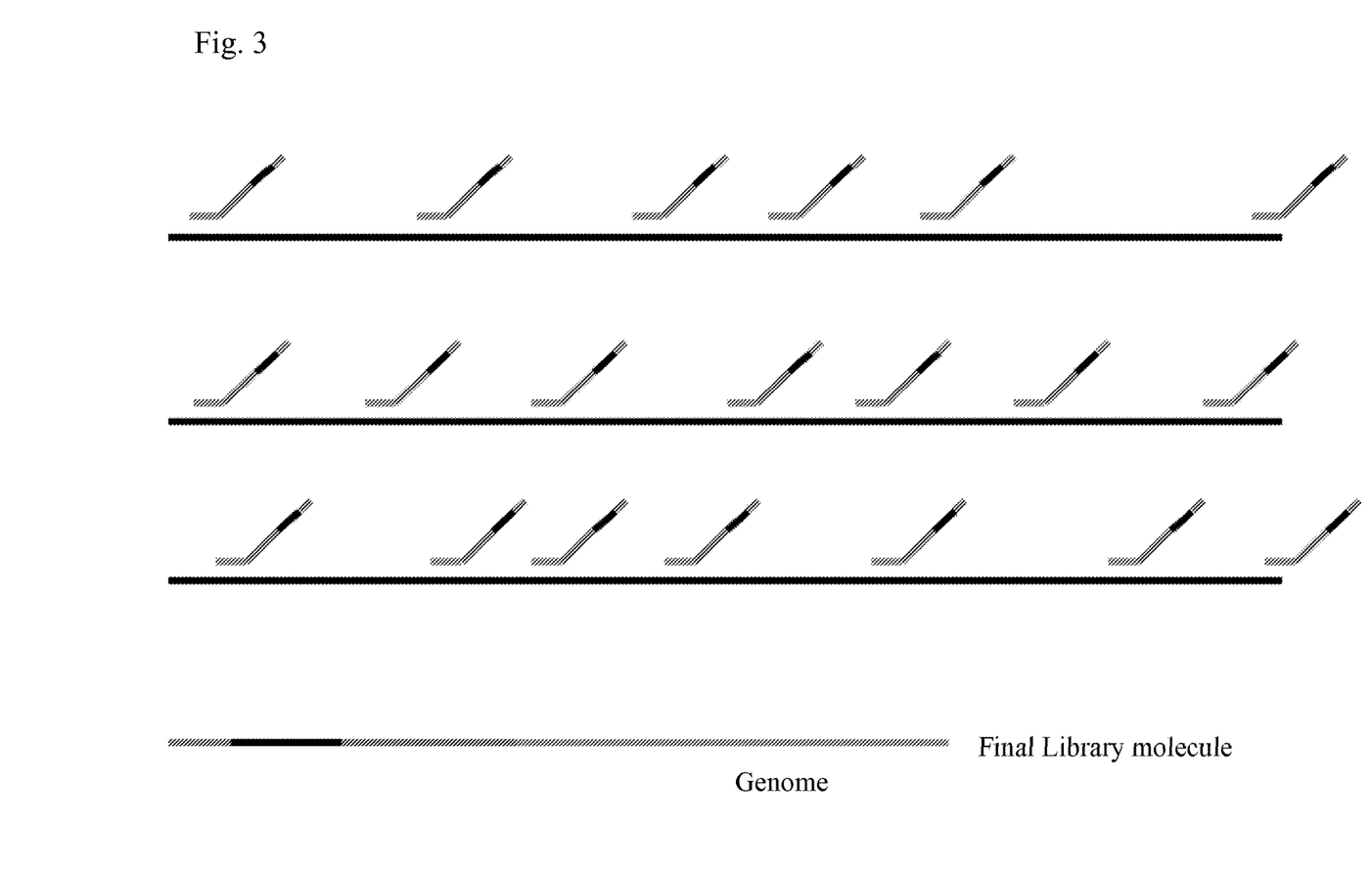
FIG. 3. A schematic diagram illustrating the generation of short reads according to the sequencing method described herein.
Figure 7:
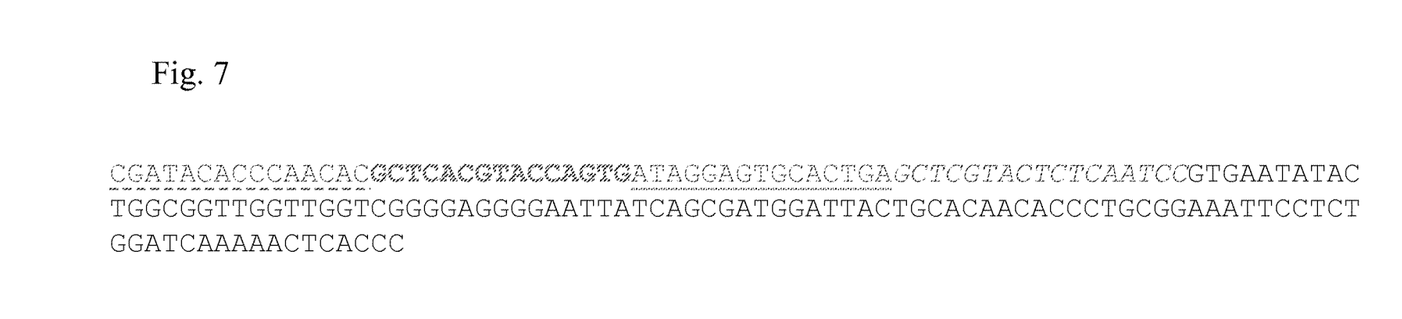
FIG. 7. E. coli genome library molecule sequenced as described in Example 1 using Ion Torrent PGM (Life Technologies Corp., Carlsbad, Calif.) and the primer shown in FIG. 6. E. coli genomic sequence (black); common sequence (italic); barcode 1 (dotted underline); barcode 2 (bold); barcode 3 (dashed underline).

Next, one can construct a DNA sequencing library from all of the long DNA molecules and ensure that all library molecules contain a barcode on the 5' end. (FIG. 3 and FIG. 7).

Figure 5:
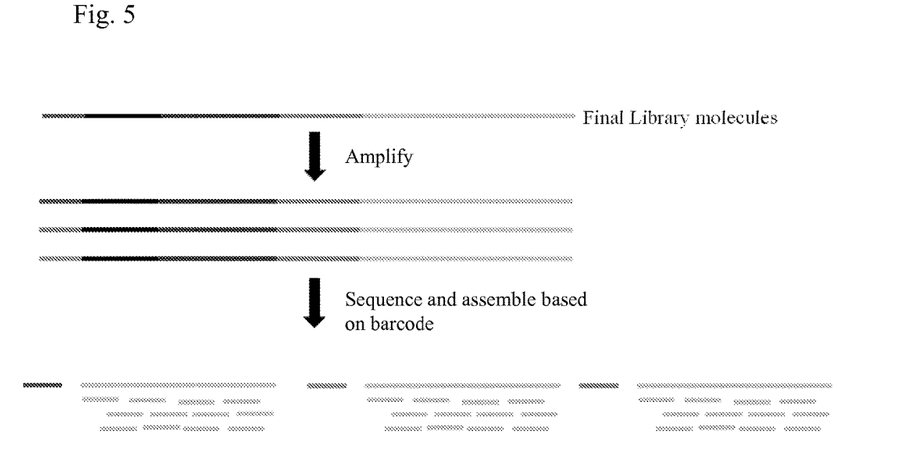
FIG. 5. A schematic diagram illustrating assembly of short read sequences to produce a synthetic long read DNA sequence.

The library may be sequenced as illustrated in FIG. 5. The sequencing process can involve sequencing a genome fragment adjacent to the primer as well as the barcode attached to the primer. All reads that have the same barcode may be identified as coming from the same large DNA molecule. One can, therefore, assemble these reads having the same barcode into a synthetic long fragment. In certain embodiments, the knowledge that a plurality of short reads come from the same large DNA molecule may be used in downstream bioinformatics analysis. In other embodiments, the short reads can be assembled into synthetic long reads that may include, for example, an entire chromosome. Even if the synthetic long reads can't be fully assembled, the relative position of the short reads will be known so that one can scaffold all the groups of reads together using bioinformatics tools.

The above description is not intended to describe each conceivable embodiment or every implementation of the methods described herein. The preceding description presents exemplary illustrative embodiments.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

For all examples, high quality DNA fragments of from 50 kb to 100 kb from tissue or blood can be isolated used the DNeasy Blood and Tissue Kit (Qiagen Inc. USA, Valencia, Calif.) following the manufacturer's instructions.

Example 1

DNA is denatured by heating to 95° C. for 5 minutes in 6×SSC with primers (Integrated DNA Technologies, Inc., Coralville, Iowa) that contain a genome binding region and a known sequence that will be used to build the barcode. The tube is immediately placed on ice to rapidly cool the sample. The sample is then purified using HIGH PURE PCR product purification kit (Roche Diagnostics, Indianapolis, Ind.) according to the manufacturer's instructions.

The DNA is then extended using PHUSION DNA Polymerase (New England Biolabs Inc., Ipswich, Mass.). To do this, the DNA is place in 1× PHUSION GC Buffer with dNTPs (Thermo Fisher Scientific Inc., Waltham, Mass.) the temperature is then slowly increased from 22° C. to 72° C. at 10° C. intervals, with a 5 minute incubation at each temperature. The sample is then purified using HIGH PURE PCR product purification kit (Roche Diagnostics, Indianapolis, Ind.) according to the manufacturer's instructions.

The purified extended DNA is then diluted into a 96 well plate. The first of the barcode adaptors is ligated to the known DNA sequence. This is done by incubating the double stranded barcode and extended DNA in 1× T4 DNA ligase buffer with High Concentration T4 DNA ligase (New England Biolabs Inc., Ipswich, Mass.) 25° C. for 10 minutes. The sample is then purified using HIGH PURE PCR product purification kit (Roche Diagnostics, Indianapolis, Ind.) according to the manufacturer's instructions. The 96 samples are then be pooled in to a single tube and then redistributed into a 96 well plate to add the second barcode. This process is then repeated to build the barcode. The final pooled samples will then be used to make a DNA library for sequencing.

Sequencing results using Ion Torrent PGM (Life Technologies Corp., Carlsbad, Calif.) are shown in FIG. 7.

Example 2

DNA is nicked by incubating the DNA in 1× CUTSMART Buffer containing Nt.CviPII (Neuer England Biolabs Inc., Ipswich, Mass.) for 60 minutes at 37° C. The enzyme is inactivated by heating the sample to 65° C. for 15 minutes. The sample is then purified using HIGH PURE PCR product purification kit (Roche Diagnostics, Indianapolis, Ind.) according to the manufacturer's instructions.

The DNA is then be treated with Antarctic Phosphatase (New England Biolabs Inc., Ipswich, Mass.) by incubating the DNA in 1× Antarctic Phosphatase Reaction Buffer for 60 minutes at 37° C. The enzyme is inactivated by heating the sample to 70° C. for 5 minutes. The sample is then purified using HIGH PURE PCR product purification kit (Roche Diagnostics, Indianapolis, Ind.) according to the manufacturer's instructions.

The purified samples are then diluted into a 96 well plate. The first of the barcode adaptors is ligated to the known DNA sequence. This is done by incubating the double stranded barcode and extended DNA in 1× T4 DNA ligase buffer with High Concentration T4 DNA ligase (New England Biolabs Inc., Ipswich, Mass.) 25° C. for 10 minutes. The sample is then purified using HIGH PURE PCR product purification kit (Roche Diagnostics, Indianapolis, Ind.) according to the manufacturer's instructions. The 96 samples are then be pooled in to a single tube and then redistributed into a 96 well plate to add the second barcode. This process is then repeated to build the barcode. The final pooled samples will then be used to make a DNA library for sequencing.

Example 3

DNA will be nicked by incubating the DNA in 1× CUTSMART Buffer containing Nt.CviPII (New England Biolabs Inc., Ipswich, Mass.) for 60 minutes at 37° C. The enzyme is inactivated by heating the sample to 65° C. for 15 minutes. The sample is then purified using HIGH PURE PCR product purification kit (Roche Diagnostics, Indianapolis, Ind.) according to the manufacturer's instructions.

The DNA is then treated with Exonuclease III (New England Biolabs Inc., Ipswich, Mass.) by incubating the DNA in 1× NEB Buffer 1 for 30 minutes at 37° C. The enzyme is inactivated by heating the sample to 70° C. for 30 minutes. The sample is then purified using HIGH PURE PCR product purification kit (Roche Diagnostics, Indianapolis, Ind.) according to the manufacturer's instructions.

The purified samples are then diluted into a 96 well plate. The first of the barcode adaptors is ligated to the known DNA sequence. This is done by incubating the double stranded barcode and extended DNA in 1× T4 DNA ligase buffer with High Concentration T4 DNA ligase (New England Biolabs Inc., Ipswich, Mass.) 25° C. for 10 minutes. The sample is then purified using HIGH PURE PCR product purification kit (Roche Diagnostics, Indianapolis, Ind.) according to the manufacturer's instructions. The 96 samples are then be pooled in to a single tube and then redistributed into a 96 well plate to add the second barcode. This process is then repeated to build the barcode. The final pooled samples will then be used to make a DNA library for sequencing.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure (s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   denaturing a plurality of genomic DNA molecules;
   attaching a plurality of primers to the denatured genomic DNA molecules, so that the genomic DNA molecules have a plurality of sites to which a primer is attached;
   extending primers attached to the DNA molecules with a polymerase that lacks strand displacement activity;
   dividing the genomic DNA molecules into a plurality of chambers;
   adding a polynucleotide barcode to one end of at least a portion of the primers;
   pooling the samples from at least a plurality of the chambers;
   redistributing the pooled samples into a second plurality of chambers;
   repeating adding a polynucleotide barcode to the end of at least a portion of the primers and pooling the samples;
   sequencing the genomic DNA and the polynucleotide barcode; and
   assembling the plurality of short reads having identical barcodes into a single long read synthetic polynucleotide sequence.

2. The method of claim 1 wherein the polymerase lacks 5'-3' exonuclease activity.

3. The method of claim 1 wherein the DNA is divided into chambers to provide 10×-40× coverage of the DNA molecule being sequenced.

4. The method of claim 1 wherein the polynucleotide barcode comprises at least five nucleotides.

5. The method of claim 1 wherein the repeating step is repeated 2-8 cycles.

6. The method of claim 1 wherein the polynucleotide barcode is added to the 5' end of at least a portion of the primers.

* * * * *

SEQUENCE LISTING

```
<160> NUMBER OF SEQ ID NOS: 8

<210> SEQ ID NO 1
<211> LENGTH: 7
<212> TYPE: DNA
<213> ORGANISM: artificial
<220> FEATURE:
<223> OTHER INFORMATION: 5' end of synthetic oligonucleotide primer

<400> SEQUENCE: 1 tttttttt                                                                  7

<210> SEQ ID NO 2
<211> LENGTH: 7
<212> TYPE: DNA
<213> ORGANISM: artificial
<220> FEATURE:
<223> OTHER INFORMATION: 5' end of synthetic oligonucleotide primer

<400> SEQUENCE: 2 cgtgcat                                                                   7

<210> SEQ ID NO 3
<211> LENGTH: 15
<212> TYPE: DNA
<213> ORGANISM: artificial
<220> FEATURE:
<223> OTHER INFORMATION: synthetic oligonucleotide primer
<220> FEATURE:
<221> NAME/KEY: misc_feature
<222> LOCATION: (1)..(2)
<223> OTHER INFORMATION: residues 1 and 2 are connected by a
      phosphothioate linkage
<220> FEATURE:
<221> NAME/KEY: misc_feature
<222> LOCATION: (2)..(3)
<223> OTHER INFORMATION: residues 2 and 3 are connected by a
      phosphothioate linkage
<220> FEATURE:
<221> NAME/KEY: misc_feature
<222> LOCATION: (13)..(14)
<223> OTHER INFORMATION: residues 13 and 14 are connected by a
      phosphothioate linkage
<220> FEATURE:
<221> NAME/KEY: misc_feature
<222> LOCATION: (14)..(15)
<223> OTHER INFORMATION: residues 14 and 15 are connected by a
      phosphothioate linkage

<400> SEQUENCE: 3
aaaaaaavvv vvvvv                                                         15

<210> SEQ ID NO 4
<211> LENGTH: 27
<212> TYPE: DNA
<213> ORGANISM: artificial
<220> FEATURE:
<223> OTHER INFORMATION: synthetic oligonucleotide primer
```

```
<220> FEATURE:
<221> NAME/KEY: misc_feature
<222> LOCATION: (1)..(2)
<223> OTHER INFORMATION: residues 1 and 2 are connected by a
      phosphothioate linkage
<220> FEATURE:
<221> NAME/KEY: misc_feature
<222> LOCATION: (2)..(3)
<223> OTHER INFORMATION: residues 2 and 3 are connected by a
      phosphothioate linkage
<220> FEATURE:
<221> NAME/KEY: misc_feature
<222> LOCATION: (18)..(24)
<223> OTHER INFORMATION: n is a, c, g, or t
<220> FEATURE:
<221> NAME/KEY: misc_feature
<222> LOCATION: (25)..(26)
<223> OTHER INFORMATION: residues 25 and 26 are connected by a
      phosphothioate linkage
<220> FEATURE:
<221> NAME/KEY: misc_feature
<222> LOCATION: (26)..(27)
<223> OTHER INFORMATION: residues 26 and 27 are connected by a
      phosphothioate linkage

<400> SEQUENCE: 4
gcacgtactc tcaatccnnn nnnnnnn                                        27

<210> SEQ ID NO 5
<211> LENGTH: 25
<212> TYPE: DNA
<213> ORGANISM: artificial
<220> FEATURE:
<223> OTHER INFORMATION: synthetic oligonucleotide primer
<220> FEATURE:
<221> NAME/KEY: misc_feature
<222> LOCATION: (1)..(2)
<223> OTHER INFORMATION: residues 1 and 2 are connected by a
      phosphothioate linkage
<220> FEATURE:
<221> NAME/KEY: misc_feature
<222> LOCATION: (2)..(3)
<223> OTHER INFORMATION: residues 2 and 3 are connected by a
      phosphothioate linkage
<220> FEATURE:
<221> NAME/KEY: misc_feature
<222> LOCATION: (18)..(22)
<223> OTHER INFORMATION: n is a, c, g, or t
<220> FEATURE:
<221> NAME/KEY: misc_feature
<222> LOCATION: (23)..(24)
<223> OTHER INFORMATION: residues 23 and 24 are connected by a
      phosphothioate linkage
<220> FEATURE:
<221> NAME/KEY: misc_feature
<222> LOCATION: (24)..(25)
<223> OTHER INFORMATION: residues 24 and 25 are connected by a
      phosphothioate linkage

<400> SEQUENCE: 5
gcacgtactc tcaatccnnn nnnnn                                          25

<210> SEQ ID NO 6
<211> LENGTH: 72
<212> TYPE: DNA
<213> ORGANISM: artificial
<220> FEATURE:
<223> OTHER INFORMATION: synthetic oligonucleotide primer
<220> FEATURE:
<221> NAME/KEY: misc_feature
<222> LOCATION: (63)..(72)
<223> OTHER INFORMATION: n is a, c, g, or t
```

```
<400> SEQUENCE: 6
cgatacaccc aacacgctca cgtaccagtg ataggagtgc actgagctcg tactctcaat      60
ccnnnnnnnn nn                                                         72

<210> SEQ ID NO 7
<211> LENGTH: 50
<212> TYPE: DNA
<213> ORGANISM: artificial
<220> FEATURE:
<223> OTHER INFORMATION: synthetic oligonucleotide primer

<400> SEQUENCE: 7
gctatgtggg ttgtgcgagt gcatggtcac tatcctcacg tgactcgagc                 50

<210> SEQ ID NO 8
<211> LENGTH: 161
<212> TYPE: DNA
<213> ORGANISM: artificial
<220> FEATURE:
<223> OTHER INFORMATION: genome library molecule and synthetic
      oligonucleotide primer

<400> SEQUENCE: 8
cgatacaccc aacacgctca cgtaccagtg ataggagtgc actgagctcg tactctcaat      60
ccgtgaatat actggcggtt ggttggtcgg ggagggaat tatcagcgat ggattactgc      120
acaacaccct gcggaaattc ctctggatca aaaactcacc c                         161
```